United States Patent
Matsushima et al.

(10) Patent No.: US 6,919,195 B2
(45) Date of Patent: Jul. 19, 2005

(54) GLUTAMINASE, GLUTAMINASE GENE, NOVEL RECOMBINANT DNA, AND PROCESS FOR MANUFACTURING GLUTAMINASE

(75) Inventors: Kenichiro Matsushima, Chiba (JP); Kotaro Ito, Chiba (JP); Yasuji Koyama, Chiba (JP)

(73) Assignee: Kikkoman Corporation, Noda (JP)

( * ) Notice: Subject to any disclaimer, the term of this patent is extended or adjusted under 35 U.S.C. 154(b) by 317 days.

(21) Appl. No.: 10/175,002

(22) Filed: Jun. 20, 2002

(65) Prior Publication Data

US 2003/0040098 A1 Feb. 27, 2003

(30) Foreign Application Priority Data

Jun. 21, 2001 (JP) .......................... 2001-187433

(51) Int. Cl.[7] ..................... C12N 9/78; C12N 15/55; C12P 13/14
(52) U.S. Cl. .................... 435/227; 435/110; 435/320.1; 435/252.3
(58) Field of Search .............................. 435/227, 320.1, 435/252.3, 110; 536/23.2

(56) References Cited

U.S. PATENT DOCUMENTS 6,312,939 B1 * 11/2001 Roberts et al. ........ 435/252.33

2002/0106782 A1   8/2002   Ito et al.
2004/0082053 A1   4/2004   Machida et al. ............ 435/226

OTHER PUBLICATIONS

Yamamoto, S., et al. (1974) J. Ferment. Technol. 52(8), 570–576.*

Yano, T., et al. (1988) J. Ferment. Technol. 66(2), 137–143.*

K. Koibuchi, et al., Applied Microbiology and Biotechnology, vol. 54, No. 1, XP–002191327, pp. 59–68, "Molecular Cloning and Characterization of a Gene Encoding Glutaminase From *Aspergillus oryzae*", Jul. 2000.

* cited by examiner

*Primary Examiner*—Charles L. Patterson, Jr.
(74) *Attorney, Agent, or Firm*—Oblon, Spivak, McClelland, Maier & Neustadt, P.C.

(57) ABSTRACT

Glutaminase which comprises (a) a protein comprising an amino acid sequence shown in SEQ ID NO: 2, or (b) a protein which comprises an amino acid sequence having deletion, substitution, or addition of one or plurality of amino acids relative to the amino acid sequence (a), and has glutaminase activity. A glutaminase gene which encodes (a) a protein comprising an amino acid sequence shown in SEQ ID NO: 2, or (b) a protein which comprises an amino acid sequence having deletion, substitution, or addition of one or a plurality of amino acids relative to the amino acid sequence (a), and has glutaminase activity. The present invention enables glutaminase to be produced efficiently and thus greatly contributes to the relevant industries.

12 Claims, No Drawings

GLUTAMINASE, GLUTAMINASE GENE, NOVEL RECOMBINANT DNA, AND PROCESS FOR MANUFACTURING GLUTAMINASE

BACKGROUND OF THE INVENTION

1. Field of the Invention

The present invention relates to a glutaminase, a glutaminase gene, a novel recombinant DNA, and a process for manufacturing a glutaminase.

2. Description of the Relevant Art

Glutaminase is an enzyme which hydrolizes L-glutamine to ammonia and L-glutamic acid, which is a umami (sweetener) flavor-enhancing component. Glutaminase plays an important role in food processing industry. It is useful, for example, in the manufacture of soy sauce or those seasonings which are produced by enzymically hydrolysing proteins. Glutaminase has been isolated from various species, and its enzymological properties and genes have been reported (e.g., in Japanese Patent Publication (Kokoku) No. 6-38748).

In the manufacture of soy sauce, and the manufacture of seasonings with the use of koji malt, in order to improve glutaminase by genetic engineering techniques and abundantly produce the enzyme, it is important to obtain the enzyme from the koji malt.

In this manner, hydrolysis products of proteins (such as soy sauce) can be easily improved in quality and provided at low prices.

SUMMARY OF THE INVENTION

It is therefore the object of the present invention to provide a koji malt-derived glutaminase, a glutaminase gene, a novel recombinant DNA, and a process for manufacturing a glutaminase.

After extensive research and analysis, the present inventors succeeded in isolating a glutaminase gene derived from *Aspergillus sojae* and determining its structure, and arrived at the present invention.

Namely, a first invention is a glutaminase according to the following (a) or (b):

(a) a protein comprising an amino acid sequence shown in SEQ ID NO: 2;

(b) a protein which comprises an amino acid sequence having deletion, substitution or addition of one or a plurality of amino acids relative to the amino acid sequence (a), and has glutaminase activity.

A second invention is a glutaminase gene which encodes a protein according to the following (a) or (b):

(a) a protein comprising an amino acid sequence shown in SEQ ID NO: 2;

(b) a protein which comprises an amino acid sequence having deletion, substitution or addition of one or a plurality of amino acids relative to the amino acid sequence (a), and has glutaminase activity.

A third invention is a glutaminase gene comprising a DNA according to the following (a) or (b):

(a) a DNA comprising a base sequence shown in SEQ ID NO: 1;

(b) a DNA which hybridizes with the DNA comprising the base sequence of (a) under stringent conditions, and which encodes a protein having glutaminase activity.

A fourth invention is a novel recombinant DNA characterized in that the above-mentioned glutaminase gene is inserted into vector DNA.

A fifth invention is a transformant or transductant containing the above-mentioned recombinant DNA.

A sixth invention is a process of manufacturing a glutaminase which comprises culturing the above-mentioned transformant or transductant on a culture medium, and collecting glutaminase from the culture product.

DESCRIPTION OF EMBODIMENTS

The present invention will be hereafter described in detail.

1. A Glutaminase and a Gene which Encodes It

The glutaminase according to the present invention is a glutaminase according to the following (a) or (b):

(a) a protein comprising an amino acid sequence shown in SEQ ID NO: 2;

(b) a protein which comprises an amino acid sequence having deletion, substitution, or addition of one or a plurality of amino acids relative to the amino acid sequence (a), and has glutaminase activity.

The protein (a) can be obtained by cloning a naturally occurring glutaminase gene derived from a chromosome DNA or cDNA of a filamentous fungi of the genus *Aspergillus*, and then introducing the clone into an appropriate vector-host system to express.

As indicated in (b), this protein may comprise an amino acid sequence having deletion, substitution, or addition of one or a plurality of amino acids relative to the amino acid sequence (a), as long as the amino acid sequence has glutaminase activity. In the present invention, "a plurality of" means usually 2 to 300, preferably 2 to 170, more preferably 2 to 50, and most preferably 2 to 10, depending on the position of the amino acid residues in the three-dimensional structure of the glutaminase protein or kind of the amino acids.

Such a mutated glutaminase, i.e., the protein (b), can be obtained by producing a mutated glutaminase gene by introducing into the base sequence of a naturally occuring glutaminase gene a mutation such as substitution, deletion, insertion, addition, or inversion, and introducing it into an appropriate vector-host system to express.

The methods of introducing the mutation into the gene include, for example, a site-specific mutagenesis, a random mutation inducing method by PCR, and a method whereby the gene is selectively cleaved and then rejoined after removal or addition of selected nucleotides.

The glutaminase gene according to the present invention is a gene containing a DNA which encodes the protein (a) or (b). The glutaminase gene according to the present invention may be a gene which hybridizes with a DNA encoding the protein (a) or (b) under stringent conditions, and which encodes a protein having glutaminase activity. In the present invention, "stringent conditions" means such conditions where the sodium concentration is 50 to 300 mM, preferably 150 mM, and the temperature is 42 to 68° C., preferably 65° C.

An example of the gene containing the DNA which encodes the protein (a) is a DNA containing the base sequence indicated by SEQ ID NO: 1. This DNA is a naturally occuring glutaminase gene.

The naturally occuring glutaminase gene can be obtained by cloning a naturally occuring gene derived from chromosome DNA or cDNA of a filamentous fungi of the genus *Aspergillus*. Gene cloning methods include, for example, one in which an appropriate probe DNA is synthesized after purifying glutaminase and determining the partial amino acid sequence, and then *Aspergillus sojae* chromosome DNA is screened using the probe DNA. Another method involves the production of an appropriate primer DNA based on a partial amino acid sequence, followed by amplification of a DNA containing fragments of the above-mentioned gene by an appropriate polymerase chain reaction (PCR) such as the 5'-RACE method or 3'-RACE method, so that the fragments are joined to produce a DNA containing the full-length gene.

Specifically, the naturally occuring glutaminase gene can be obtained as follows. Initially, *Aspergillus sojae* FERM BP-6820 is cultured, and a resultant bacterial body is frozen in liquid nitrogen, then physically milled or ground by using a mortar or the like, thereby obtaining bacterial body fragments in a fine powder form, from which an entire RNA fraction is extracted in a usual manner. In the extraction procedure, commercially available RNA extraction kits can be used.

Alternatively, an RNA may be collected from the resultant RNA liquid extract by ethanol precipitation, and then an RNA with a poly A chain may be fractionated in a usual manner. In this fractionation procedure, a commercially available Oligo dT column can be used.

Primers for use in PCR are synthesized by referring to the DNA sequence in SEQ ID NO: 2. Using this primer DNA and the RNA obtained in the above-described manner, a DNA containing fragments of the gene is amplified by an appropriate RT-PCR reaction such as the 5'-RACE method and the 3'-RACE method, and a DNA containing the full-length gene is obtained by joining these fragments. In the partial cDNA synthesizing procedure by the 5'-RACE method and 3'-RACE method, commercially available kits may be used.

Using the above cDNA as a template, PCR is performed with the synthesized primer complementary to the 5'-end sequence and the 3'-end sequence, thereby amplifying the DNA. The amplified DNA can be cloned according to conventional methods.

The amplified DNA is inserted into an appropriate vector to obtain a recombinant DNA. For cloning, a commercially available kit such as TA Cloning Kit (Invitrogen Corporation), commercially available plasmid vector DNAs such as pUC119 (Takara Shuzo Co., Ltd.), pBR322 (Takara Shuzo Co., Ltd.), and pBluescript SK+ (Stratagene), and a commercially available bacteriophage vector DNA such as λ EMBL3 (Stratagene), or the like can be used.

By using the resultant recombinant DNA, a transformant or a transductant is obtained by transforming or transducing *Escherichia coli* K-12, preferably *Escherichia coli* JM109 (Takara Shuzo Co., Ltd.), or XL-Blue (Stratagene), for example. The transformation can be performed by D. M. Morrison's method (Methods in Enzymology, 68, 326–331, 1979), for example. The transduction, on the other hand, can be performed by B. Hohn's method (Methods in Enzymology, 68, 299–309, 1979), for example. As a host cell, in addition to *Escherichia coli,* other microorganisms such as bacteria, yeasts, filamentous fungus and actinomycete, and animal cells may be used.

The entire base sequence (see SEQ ID NO: 1) of the thus amplified DNA can be analyzed by, for example, Li-COR MODEL 4200L Sequencer (purchased from ALOKA CO., LTD.), 370DNA Sequence System (PerkinElmer Inc.), or CEQ2000XL DNA Analysis System (Beck man Coulter). By comparing the base sequence with information about the partial amino acid sequence, it can be determined whether or not naturally occuring glutaminase gene was obtained.

And by analyzing the naturally occuring glutaminase gene, the amino acid sequence of the translated polypeptide, i.e., the protein (a), can be determined.

2. Process of Manufacturing Glutaminase

When manufacturing the glutaminase according to the present invention, initially a recombinant DNA containing the glutaminase gene is produced. A transformant or transductant containing that recombinant DNA is then produced and cultured, and glutaminase can be collected from the cultured product.

In order to manufacture the protein having glutaminase activity by using the glutaminase gene according to the present invention, it is necessary to select an appropriate vector-host system. As such a system, there can be mentioned, e.g., a system of pST14 (Unkles et al., 1989, Mol. Gen. Genet., 218, 99–104) and a filamentous fungi (*Aspergillus sojae, Aspergillus oryzae, Aspergillus nidulans, Aspergillus niger, Penicillium chrysogenum*, etc.), a system of a yeast expression vector pYES2 (Invitrogen) and a yeast *Saccharomyces cerevisiae*, and a system of an *Escherichia coli* expression vector pTE (Stratagene) and *Escherichia coli*. It is preferable to use a filamentous fungi or yeast system in which there occurs sugar chain addition to the protein.

The recombinant DNA can be obtained by inserting the glutaminase gene into an appropriate vector. As the vector, commercially available products can be used, such as yeast expression vectors pYES2, pYD1 (Invitrogen), pUR123 (Takara Shuzo Co., Ltd.), pYEX-BX, pYEX-S1, pYEX-4T (CLONTECH), *Escherichia coli* expression vector pSET (Invitrogen), and pTE (Stratagene), for example.

Thereafter, the recombinant DNA is transformed or transducted into a host cell. The transduction into the yeast can be performed by, for example, the method of Becker D M. et al. (Methods in Enzymology, 194, 182–187, 1991). As the host cell, in addition to the *Escherichia coli* and yeast, there can be used microorganisms such as other bacteria, filamentous fungus, and actinomycetes, or animal cells.

There is thus obtained a transformant or transductant with a glutaminase production capacity. Though the transformant or transductant may be cultured by the conventional solid culture method, it is preferable to adopt the liquid culture method as much as possible.

When a yeast is used as a host, general eutrophic media such as YPD media and YM media may be used. When a selective medium is used in view of the genetic properties of the host, an SD medium being a minimal medium can be used. When using the selective medium, since the selection pressure differs depending on the host-vector system used, amino acids or nucleic acids other than the selection pressure, for example, are added to the minimal medium, in accordance with the host's genetic requirement as needed.

In addition, inorganic salts, saccharide materials, vitamins, etc., may be added to the medium as necessary. The initial pH of the medium is appropriately adjusted to pH 6 to 9. Depending on the vector used, the expression of the protein can be controlled. When using such a vector, glutaminase can be induced by adding an inducer appropriate for the vector, such as galactose or copper ions.

When the yeast is cultured, there should preferably be used such methods as an aeration-agitation submerged culture, shaking culture, static culture, etc., at temperatures of 25 to 35° C., preferably at more or less 30° C., for 24 to 48 hours.

The glutaminase that expressed can be purified by a method partly modified from the method described in Japanese Patent Application Laid-Open (Kokai) No. 11-332553.

In the case of the yeast, after the transformed yeast is cultured by the above-mentioned appropriate method, the culture solution is centrifuged to obtain a yeast body. After the cell wall is sufficiently lysed by the addition of a cell-wall lysing enzyme to the yeast body, a supernatant liquid is obtained by centrifugation. Ammonium sulfate is then added to the supernatant liquid to thereby salt out, and the liquid is further centrifuged to remove insoluble proteins, thereby obtaining a crude enzyme solution containing glutaminase.

From the crude enzyme solution is purified a glutaminase active fraction by means of the Phenyl Sepharose column, DEAE-Sepharose column, a gel filtration column, and HPLC, thereby obtaining a purified glutaminase.

The genetic engineering method according to the present invention can be performed according to the descriptions in "Molecular Cloning: A Laboratory Manual $2^{nd}$ edition". (1989), Cold Spring Harbor Laboratory Press, ISBN 0-8769-309-6, and "Current Protocols in Molecular Biology" (1989), John Wiley & Sons, Inc., ISBN 0-471-50338-X, for example.

EXAMPLES

The present invention will be hereafter described in greater detail by way of examples.

Example 1

Acquisition of a Glutaminase cDNA
(1) Retrieval of a Glutaminase Homologous Gene in a Bacterium of the Genus *Aspergillus*

After searching the koji mold EST library of the International Patent Organism Depositary at the National Institute of Advanced Science and Technology for a gene which is highly homologous to a known glutaminase gene derived from *Cryptococcus* (Japanese Patent Application No. 2000-270371), an EST clone Contig Mix0010110003775_1 comprising 711 bases was obtained. The clone was presumed to be a fragment of the glutaminase gene, and a cDNA of the gene was cloned.
Extraction of the Entire RNA from *Aspergillus sojae*

Spores of the *Aspergillus sojae* FERM BP-6820 were inoculated into 50 ml of a soybean power medium (3% soybean powder, 1% $KH_2PO_4$, pH6.0) to a density of $3 \times 10^5$/ml, and the spores were shake-cultured in a 150 ml Erlenmeyer flask at 30° C. for 48 hours, at 150 r.p.m.

A resultant culture solution was filtered by Miracloth (Calbiochem) to thereby collect a bacterial body. After washing the collected bacteria with sterilized water, it was frozen in liquid nitride and then physically ground in a mortar, thereby obtaining fine powdery bacterial fragments. From the bacterial fragments were extracted an entire RNA by means of ISOGEN (Nippon Gene Co., Ltd.). The entire procedure was performed in accordance with the attached protocol.
(2) Acquisition of a Glutaminase cDNA by the RACE Method From about 200 μg of the entire RNA thus obtained, 4 μg of mRNA was obtained by using the Oligotex-dT30<Super> mRNA Purification Kit (Takara Shuzo Co., Ltd.). Of the mRNA, 1 μg was subjected to 5'-RACE and 3'-RACE performed by using the Marathon cDNA Amplification Kit (Clontech) and Advantage cDNA PCR kit (Clontech). As primers for the RACE method, oligo DNAs respectively expressed by SEQ ID NOS: 3–6 were synthesized, namely antisense primers (SEQ ID NOS: 3 and 4) for the EST clone CONTIG MIX0010110003775_1 for the 5'-RACE and sense primers (SEQ ID NOS: 5 and 6) for performing the 3'-RACE. The entire procedure was performed in accordance with the attached protocol. As PCR apparatus, there was used the GeneAmp5700 DNA detection system (PerkinElmer). As a result, amplification of about 1.7 kb of a DNA fragment corresponding to the glutaminase cDNA 5'-region, and about 0.8 kb of a DNA fragment corresponding to the 3'-region were confirmed.

The amplified DNA fragments were separated on a 0.7% agarose gel, and extracted by using the QIAquick Gel Extraction Kit (QIAGEN). The procedure was in accordance with the attached protocol. The extracted DNA fragment was incorporated into a pCR2.1-TOPO vector by using the TOPO TA Cloning Kit (Invitrogen). The resultant recombinant plasmid was subjected to sequence reaction by using the Thermo Sequence Cycle Sequencing Kit (Amersham Pharmacia Biotech), and the base sequence was determined by the LI-COR MODEL4200L sequencer (purchased from Aloka). As a result, the DNA sequence of approximately 1.9-kb open reading frame (ORF) indicated by SEQ ID NO: 1 was determined, and it became clear that the EST clone CONTIG MIX0010110003775_1 was a partial fragment thereof.

This DNA encoded a protein comprising 643 amino acids. This amino acid sequence is described in SEQ ID NO: 2. Furthermore, a homology search was performed on a known amino acid sequence database with regard to this amino acid sequence. For the homology search, NCBI BLAST (http://www.ncbi.nlm.nih.gov/BLAST/) was used. As a result, there was no known protein matching the above-mentioned ORF.

However, when a homology search was performed with respect to a glutaminase derived from *Cryptococcus albidus* and *Cryptococcus nodaensis,* homology was recognized in a region which is expected to be an active center, which suggested that the glutaminase was encoded by the ORF.

PCR was performed by using as a template the cDNA which was produced during a 5'-RACE, whereby the full-length cDNA of glutaminase was cloned. As a primer, oligo DNA indicated by SEQ ID NOS: 7 and 8 were used. The resultant amplified DNA fragment of about 2.1 kb was extracted by the above-mentioned method and incorporated into the pCR2.1-TOPO vector by using the TOPO TA Cloning Kit (Invitrogen), thereby obtaining a recombinant plasmid pASgln containing the full-length cDNA of glutaminase.

The base sequence of the recombinant plasmid pASgln was again analyzed to determine the base sequence of the glutaminase cDNA (SEQ ID NO: 1).

The full-length glutaminase cDNA, i.e., the plasmid pASgln containing the base sequence indicated by base Nos. 1 to 1932 of SEQ ID NO: 1, is deposited with the International Patent Organism Depositary at National Institute of Advanced Science and Technology, as FERM BP-7634.

Example 2

Expression of Glutaminase cDNA

The above-mentioned plasmid pASgln was subjected to an enzyme treatment with restriction enzymes Bam HI and Sph I (both by Takara Shuzo Co., Ltd.). Then, it was subjected to 0.7% agarose gel electrophoresis. Thereafter, DNA fragments of a desired size (about 2.0 kbp) were sliced and purified.

These DNA fragments were incorporated into a yeast expression vector pYES2 (Invitrogen) which has been subjected to an enzyme treatment by the above-mentioned restriction enzyme, to thereby produce a recombinant plasmid pYES-ASgln. This recombinant plasmid is capable of inducing a target protein glutaminase to express. As a host, the attached INVSc1 (Genotype: MATa, his3Δ1, leu2, trp1-289, ura3-52/MATα, his3Δ1, leu2, trp1-289, ura3-52) was used, and the host yeast was transformed by the above-mentioned plasmid pYES-ASgln by the lithium acetate method. As a selective medium, there was used 0.67% Yeast Nitrogenbase without amino acids (Difco), 2% raffinose (Wako Pure Chemicals Industries, Ltd.), and 0.192% Yeast Synthetic Dropout Medium Supplement without uracil (SIGMA). The lithium acetate method was performed in accordance with the description in "Tanpakushitsu Jikken Purotokoru—Kino Kaiseki-hen—" ("Protein Experiment Protocol—Function Analysis—") (A supplement to a magazine Saibo Kogaku (Cell Technology; Shujun-sha).

Thereafter, the resultant transformant was used to express a protein according to the protocol attached to the pYES2 vector (Invitrogen). The transformant was transplanted from a colony into a 20 ml of the selective medium by using a 200-ml Erlenmeyer flask with bumps, and shake-cultured at 30° C., 140 r.p.m., for about 14 hours, thereby obtaining a seed culture.

The turbidity ($OD_{600}$) of the seed culture was then measured, and the seed culture was inoculated into a protein expression-inducing medium such that the initial turbidity is $OD_{600}$=0.4. For culturing in the protein expression-inducing medium, a 500 ml Sakaguchi flask was used, and a shaking culture was performed in 50 ml of the medium at 30° C., 140 r.p.m. As a protein expression-inducing medium, there were used a 1% Yeast Extract (Difco), a 2% Poly Peptone (Nippon Seiyaku K.K.), a 1% raffinose and a 2% galactose (both SIGMA). A centrifuged and collected yeast body was suspended in distilled water and supplied as an enzyme solution.

Glutaminase activity was measured by a method partly modified from the method described in Japanese Patent Application Laid-Open (Kokai) No. 11-332553. Specifically, 500 μl of 0.2 M phosphoric acid buffer solution (pH 6.5) and 500 μl of the enzyme solution were added to 250 μl of 2% (W/V) L-glutamine solution and reacted at 37° C. for 30 minutes. The reaction was then terminated by adding 250 μl of 0.75 N perchloric acid solution, and the reaction solution was neutralized by adding 125 μl of 1.5 N sodium hydroxide solution. This reaction solution was centrifuged (10000 r.p.m., 10 min), and to 100 μl of the supernatant liquid were added 1.0 ml of 0.1 M hydroxylamine hydrochloride buffer solution (pH 8.0), 1.0 ml of 20 mM NAD+ solution (Oriental Yeast Co., Ltd.), and 50 μl of 500 units/ml L-glutamic acid dehydrogenase solution (SHIGMA). The supernatant solution was then reacted at 37° C. for 30 minutes, and the absorbance at 340 nm was measured by a spectrophotometer. Under these conditions, a single unit (U) of glutaminase activity was defined as the amount of enzyme which generates 1 μmol of glutamic acid per minute.

The result of measuring glutaminase activity of the transformant is shown in Table 1. The values in the table indicate glutaminase activity per 1 ml of the culture liquid (mU/ml) 24 hours after the start of culturing ($OD_{600}$=15). The designation "pYES2" indicates the transformant by plasmid pYES2, and the designation "pYES-ASgln" indicates the transformant by plasmid pYES-ASgln. The signs "−" and "+" indicate induction by a protein expression non-inducing medium containing no galactose and by a protein expression-inducing medium containing galactose, respectively.

TABLE 1

| Plasmid/galactose | − | + |
|---|---|---|
| PYES2 | 0.33 | 2.50 |
| PYES-Asgln | 4.64 | 32.87 |

When cultured on the protein expression-inducing medium containing galactose, the transformant by the plasmid pYES-ASgln was higher in glutaminase activity than the transformant by the plasmid pYES2. On the other hand, when cultured in the protein expression non-inducing medium containing no galactose, the transformant by the plasmid pYES-ASgln showed no increase in glutaminase activity. This indicated that the glutaminase activity of the transformant by the plasmid pYES-ASgln derived from the introduced glutaminase gene (Table 1). When the INVSc1 was used as the host to express glutaminase, too, the glutaminase activity expressed on the surface of the yeast body, as in the case of the bacterium of the genus *Aspergillus*.

Thus, in accordance with the present invention, glutaminase can be efficiently manufactured. The present invention therefore has great industrial applicability.

What is claimed is:

1. An isolated nucleic acid comprising a polynucleotide which hybridizes to the complement of SEQ ID NO: 1 under stringent conditions, and which encodes a protein having glutaminase activity;

wherein stringent conditions comprise hybridization in 150 mM sodium at a temperature of 65° C.

2. The nucleic acid of claim 1, which encodes the polypeptide of SEQ ID NO: 2 or a fragment of SEQ ID NO: 2 having glutaminase activity.

3. The nucleic acid of claim 1 which comprises SEQ ID NO: 1.

4. An isolated vector comprising the nucleic acid of claim 1.

5. An isolated host cell comprising the nucleic acid of claim 1.

6. The isolated host cell of claim 5 which is selected from the group consisting of a fungi, yeast and bacterium.

7. An isolated polypeptide which has glutaminase activity, which is encoded by a polynucleotide which hybridizes to the complement of SEQ ID NO: 1 under stringent conditions, wherein stringent conditions comprise hybridization in 150 mM sodium at a temperature of 65° C.

8. The polypeptide of claim 7 which comprises SEQ ID NO: 2 or a fragment of SEQ ID NO: 2.

9. The polypeptide of claim 7 which is encoded by SEQ ID NO: 1.

10. A method for producing an isolated polypeptide which has glutaminase activity comprising:

expressing the isolated nucleic acid of claim 1 and recovering the polypeptide expressed by said nucleic acid.

11. The method of claim 10 further comprising purifying the polypeptide having glutaminase activity.

12. A method for producing L-glutamic acid comprising:

contacting a substrate containing L-glutamine with the polypeptide of claim 7 for a time and under conditions suitable for hydrolysis of L-glutainine into L-glutamic acid.

* * * * *

SEQUENCE LISTING

<160> NUMBER OF SEQ ID NOS: 8

<210> SEQ ID NO 1
<211> LENGTH: 1932
<212> TYPE: DNA
<213> ORGANISM: Aspergillus sojae
<220> FEATURE:
<221> NAME/KEY: CDS
<222> LOCATION: (1)..(1932)
<223> OTHER INFORMATION:

<400> SEQUENCE: 1

```
atg ttt ctt agt aca ctc ctc tca ctg gcg gcg gtc gtt gcc ggc gct      48
Met Phe Leu Ser Thr Leu Leu Ser Leu Ala Ala Val Val Ala Gly Ala
1               5                   10                  15 gcc atc ccc aat ggc cag acg ctt tct ctc aat gac att cct tac tat      96
Ala Ile Pro Asn Gly Gln Thr Leu Ser Leu Asn Asp Ile Pro Tyr Tyr
```

-continued

|  |  | 20 |  |  |  |  | 25 |  |  |  |  | 30 |  |  |  |  |
|---|---|---|---|---|---|---|---|---|---|---|---|---|---|---|---|---|
| gtg | agc | ggc | att | cct | gtg | tca | act | ttg | caa | ggg | tac | aat | gcc | tct | gca | 144 |
| Val | Ser | Gly | Ile | Pro | Val | Ser | Thr | Leu | Gln | Gly | Tyr | Asn | Ala | Ser | Ala |  |
|  |  | 35 |  |  |  |  | 40 |  |  |  |  | 45 |  |  |  |  |

```
tat gct gct ttg aca aag gga ata gat ttg gtg cca tta act gtc att    192
Tyr Ala Ala Leu Thr Lys Gly Ile Asp Leu Val Pro Leu Thr Val Ile
         50                  55                  60 cct gta act cct acc acg aac ttg gag tcg ctg cta tcg gac tat gtt    240
Pro Val Thr Pro Thr Thr Asn Leu Glu Ser Leu Leu Ser Asp Tyr Val
 65                  70                  75                  80 gaa cgc gat gat gtc ttc cag ccg gct ttt ctg cgt gca gtc tat ctc    288
Glu Arg Asp Asp Val Phe Gln Pro Ala Phe Leu Arg Ala Val Tyr Leu
                     85                  90                  95 aca gct tcc act gct gat gac att gac tcc caa ctg agc aat tat gcg    336
Thr Ala Ser Thr Ala Asp Asp Ile Asp Ser Gln Leu Ser Asn Tyr Ala
                 100                 105                 110 tca att ctc aag tct tcc ggc acc gac gtg ctg ctg gtt gat tca gaa    384
Ser Ile Leu Lys Ser Ser Gly Thr Asp Val Leu Leu Val Asp Ser Glu
             115                 120                 125 gta cac acc gct tcg tca gat tcc aca atc aca gcg cag ttg acc aaa    432
Val His Thr Ala Ser Ser Asp Ser Thr Ile Thr Ala Gln Leu Thr Lys
         130                 135                 140 gag ctg ccg agt ggg cct tat ttt gtc tcc ttg tat act gga gag gtg    480
Glu Leu Pro Ser Gly Pro Tyr Phe Val Ser Leu Tyr Thr Gly Glu Val
145                 150                 155                 160 ttt aga gcg tac cgg ttg tac cct gac gac aac cta gct ttc att caa    528
Phe Arg Ala Tyr Arg Leu Tyr Pro Asp Asp Asn Leu Ala Phe Ile Gln
                 165                 170                 175 gca gga atc agt gac gag aag gga ggt gtc ctg ccc cta cca gcc gtg    576
Ala Gly Ile Ser Asp Glu Lys Gly Gly Val Leu Pro Leu Pro Ala Val
             180                 185                 190 aca gaa aac gcg atg acc aaa gac gtt gcc gtg cct tca cgt ctc tat    624
Thr Glu Asn Ala Met Thr Lys Asp Val Ala Val Pro Ser Arg Leu Tyr
         195                 200                 205 tat aca ccg acc gca gaa aag cca tta gcc ggt ctg agg tta ggt gtc    672
Tyr Thr Pro Thr Ala Glu Lys Pro Leu Ala Gly Leu Arg Leu Gly Val
     210                 215                 220 aag gat atc tac cac gtt aaa ggt ctc aag acg agt ggc ggc agt cgc    720
Lys Asp Ile Tyr His Val Lys Gly Leu Lys Thr Ser Gly Gly Ser Arg
225                 230                 235                 240 tcc tat tat tat tta tac gga act cag aat gtc act gcc cca tct att    768
Ser Tyr Tyr Tyr Leu Tyr Gly Thr Gln Asn Val Thr Ala Pro Ser Ile
                 245                 250                 255 cag aga ctg ttg gac tta ggc gcg gtc ttt gtc ggt aaa act ggg acc    816
Gln Arg Leu Leu Asp Leu Gly Ala Val Phe Val Gly Lys Thr Gly Thr
             260                 265                 270 gtt cag ttt gct aac ggt gat cga cct act gcc gac tgg gtg gat ttc    864
Val Gln Phe Ala Asn Gly Asp Arg Pro Thr Ala Asp Trp Val Asp Phe
         275                 280                 285 cac tgt cca ttc aac caa cgc gga gaa gga tat cag gca cct agc ggt    912
His Cys Pro Phe Asn Gln Arg Gly Glu Gly Tyr Gln Ala Pro Ser Gly
     290                 295                 300 tcc tcc tcc ggc tca ggt gtg gct att gca gcc tac gac tgg ttg gac    960
Ser Ser Ser Gly Ser Gly Val Ala Ile Ala Ala Tyr Asp Trp Leu Asp
305                 310                 315                 320 ctt gct gtc ggt agt gac act ggc ggt tca atg cgt tcc cca gct gca    1008
Leu Ala Val Gly Ser Asp Thr Gly Gly Ser Met Arg Ser Pro Ala Ala
                 325                 330                 335 gtt caa ggg ata tat ggc aac agg cca tct act ggc gct atc tct cta    1056
```

```
Val Gln Gly Ile Tyr Gly Asn Arg Pro Ser Thr Gly Ala Ile Ser Leu
            340                 345                 350 gat cat gtc tta cct ctc tcg ccg gct ctg gat aca gcg ggc gtc ttt      1104
Asp His Val Leu Pro Leu Ser Pro Ala Leu Asp Thr Ala Gly Val Phe
        355                 360                 365 gcc cga agt gcc tca cta tgg tcc cat act gtg caa gct tgg tat cct      1152
Ala Arg Ser Ala Ser Leu Trp Ser His Thr Val Gln Ala Trp Tyr Pro
370                 375                 380 cat ctc cag cac aat ttt acg tcc ttc cct cgg cag ctg ctc cta gcc      1200
His Leu Gln His Asn Phe Thr Ser Phe Pro Arg Gln Leu Leu Leu Ala
385                 390                 395                 400 ggt ggt gga tgg gat ggt aaa ggc atc agt ccc gag gcc cat cag agt      1248
Gly Gly Gly Trp Asp Gly Lys Gly Ile Ser Pro Glu Ala His Gln Ser
                405                 410                 415 ctt acc aca ttc aca cgt ggg ctt gag gca ttc ctc gga aca aac cat      1296
Leu Thr Thr Phe Thr Arg Gly Leu Glu Ala Phe Leu Gly Thr Asn His
            420                 425                 430 acc aat gtc gac gtg tcg cag cga tgg ctt gac aca cac tct ccc acc      1344
Thr Asn Val Asp Val Ser Gln Arg Trp Leu Asp Thr His Ser Pro Thr
        435                 440                 445 aca cca agc ctg gaa gag atg ctc aac ctg acc tat gcc aca ctt act      1392
Thr Pro Ser Leu Glu Glu Met Leu Asn Leu Thr Tyr Ala Thr Leu Thr
    450                 455                 460 tct gtg gat cag ttc aac cac cta gcc gtc cct ctc ttt gct gac tat      1440
Ser Val Asp Gln Phe Asn His Leu Ala Val Pro Leu Phe Ala Asp Tyr
465                 470                 475                 480 aaa gcc gtc cac cgc ggt cgt cag cct ttc att aac ccc ggc cca tta      1488
Lys Ala Val His Arg Gly Arg Gln Pro Phe Ile Asn Pro Gly Pro Leu
                485                 490                 495 gcg cgt tgg cag tgg ggc cag gcg aat ggc gga aac acc tcg tac gat      1536
Ala Arg Trp Gln Trp Gly Gln Ala Asn Gly Gly Asn Thr Ser Tyr Asp
            500                 505                 510 gca gct ctg cgc aac atg act act ttc cga aac tgg tgg gag aag tcc      1584
Ala Ala Leu Arg Asn Met Thr Thr Phe Arg Asn Trp Trp Glu Lys Ser
        515                 520                 525 ggg tat ggt cag tcc gat aat gcc tct tgc tcc agg tcg ctt ttc gtc      1632
Gly Tyr Gly Gln Ser Asp Asn Ala Ser Cys Ser Arg Ser Leu Phe Val
    530                 535                 540 agt gtg tat tcg gtc ggc acc act gac tac cgt aac caa tat tat gag      1680
Ser Val Tyr Ser Val Gly Thr Thr Asp Tyr Arg Asn Gln Tyr Tyr Glu
545                 550                 555                 560 gcg ccc act aca ccc cca ctg gga ttc tcg atc gga cgc atc gcg gta      1728
Ala Pro Thr Thr Pro Pro Leu Gly Phe Ser Ile Gly Arg Ile Ala Val
                565                 570                 575 tta ggt gga gca cct gag gtt gtt gtt cct gtg gga gag tcc cca tac      1776
Leu Gly Gly Ala Pro Glu Val Val Val Pro Val Gly Glu Ser Pro Tyr
            580                 585                 590 aat agt act atc tct ttg cag acc gag tat ttg ccg gtc agt gtt gcg      1824
Asn Ser Thr Ile Ser Leu Gln Thr Glu Tyr Leu Pro Val Ser Val Ala
        595                 600                 605 ctg cag atg gcg cga gga tgt gac cat gtt ctg gct tcc ttg gtc gct      1872
Leu Gln Met Ala Arg Gly Cys Asp His Val Leu Ala Ser Leu Val Ala
    610                 615                 620 ggc ctt gag aag aag ggc gtc ctc cga cct gtc agt acc ggc tct cgc      1920
Gly Leu Glu Lys Lys Gly Val Leu Arg Pro Val Ser Thr Gly Ser Arg
625                 630                 635                 640 cta tac tcc taa                                                       1932
Leu Tyr Ser
```

<210> SEQ ID NO 2
<211> LENGTH: 643
<212> TYPE: PRT
<213> ORGANISM: Aspergillus sojae

<400> SEQUENCE: 2

```
Met Phe Leu Ser Thr Leu Leu Ser Leu Ala Val Val Ala Gly Ala
1               5                   10                  15

Ala Ile Pro Asn Gly Gln Thr Leu Ser Leu Asn Asp Ile Pro Tyr Tyr
            20                  25                  30

Val Ser Gly Ile Pro Val Ser Thr Leu Gln Gly Tyr Asn Ala Ser Ala
            35                  40                  45

Tyr Ala Ala Leu Thr Lys Gly Ile Asp Leu Val Pro Leu Thr Val Ile
        50                  55                  60

Pro Val Thr Pro Thr Thr Asn Leu Glu Ser Leu Ser Asp Tyr Val
65                  70                  75                  80

Glu Arg Asp Asp Val Phe Gln Pro Ala Phe Leu Arg Ala Val Tyr Leu
                85                  90                  95

Thr Ala Ser Thr Ala Asp Asp Ile Asp Ser Gln Leu Ser Asn Tyr Ala
            100                 105                 110

Ser Ile Leu Lys Ser Ser Gly Thr Asp Val Leu Leu Val Asp Ser Glu
        115                 120                 125

Val His Thr Ala Ser Ser Asp Ser Thr Ile Thr Ala Gln Leu Thr Lys
    130                 135                 140

Glu Leu Pro Ser Gly Pro Tyr Phe Val Ser Leu Tyr Thr Gly Glu Val
145                 150                 155                 160

Phe Arg Ala Tyr Arg Leu Tyr Pro Asp Asn Leu Ala Phe Ile Gln
                165                 170                 175

Ala Gly Ile Ser Asp Glu Lys Gly Val Leu Pro Leu Pro Ala Val
            180                 185                 190

Thr Glu Asn Ala Met Thr Lys Asp Val Ala Val Pro Ser Arg Leu Tyr
        195                 200                 205

Tyr Thr Pro Thr Ala Glu Lys Pro Leu Ala Gly Leu Arg Leu Gly Val
    210                 215                 220

Lys Asp Ile Tyr His Val Lys Gly Leu Lys Thr Ser Gly Gly Ser Arg
225                 230                 235                 240

Ser Tyr Tyr Tyr Leu Tyr Gly Thr Gln Asn Val Thr Ala Pro Ser Ile
                245                 250                 255

Gln Arg Leu Leu Asp Leu Gly Ala Val Phe Val Gly Lys Thr Gly Thr
            260                 265                 270

Val Gln Phe Ala Asn Gly Asp Arg Pro Thr Ala Asp Trp Val Asp Phe
        275                 280                 285

His Cys Pro Phe Asn Gln Arg Gly Glu Gly Tyr Gln Ala Pro Ser Gly
    290                 295                 300

Ser Ser Ser Gly Ser Gly Val Ala Ile Ala Ala Tyr Asp Trp Leu Asp
305                 310                 315                 320

Leu Ala Val Gly Ser Asp Thr Gly Gly Ser Met Arg Ser Pro Ala Ala
                325                 330                 335

Val Gln Gly Ile Tyr Gly Asn Arg Pro Ser Thr Gly Ala Ile Ser Leu
            340                 345                 350

Asp His Val Leu Pro Leu Ser Pro Ala Leu Asp Thr Ala Gly Val Phe
        355                 360                 365

Ala Arg Ser Ala Ser Leu Trp Ser His Thr Val Gln Ala Trp Tyr Pro
    370                 375                 380
```

His Leu Gln His Asn Phe Thr Ser Phe Pro Arg Gln Leu Leu Leu Ala
385                 390                 395                 400

Gly Gly Gly Trp Asp Gly Lys Gly Ile Ser Pro Glu Ala His Gln Ser
            405                 410                 415

Leu Thr Thr Phe Thr Arg Gly Leu Glu Ala Phe Leu Gly Thr Asn His
        420                 425                 430

Thr Asn Val Asp Val Ser Gln Arg Trp Leu Asp Thr His Ser Pro Thr
    435                 440                 445

Thr Pro Ser Leu Glu Glu Met Leu Asn Leu Thr Tyr Ala Thr Leu Thr
450                 455                 460

Ser Val Asp Gln Phe Asn His Leu Ala Val Pro Leu Phe Ala Asp Tyr
465                 470                 475                 480

Lys Ala Val His Arg Gly Arg Gln Pro Phe Ile Asn Pro Gly Pro Leu
            485                 490                 495

Ala Arg Trp Gln Trp Gly Gln Ala Asn Gly Gly Asn Thr Ser Tyr Asp
        500                 505                 510

Ala Ala Leu Arg Asn Met Thr Thr Phe Arg Asn Trp Trp Glu Lys Ser
    515                 520                 525

Gly Tyr Gly Gln Ser Asp Asn Ala Ser Cys Ser Arg Ser Leu Phe Val
530                 535                 540

Ser Val Tyr Ser Val Gly Thr Thr Asp Tyr Arg Asn Gln Tyr Tyr Glu
545                 550                 555                 560

Ala Pro Thr Thr Pro Pro Leu Gly Phe Ser Ile Gly Arg Ile Ala Val
            565                 570                 575

Leu Gly Gly Ala Pro Glu Val Val Pro Val Gly Glu Ser Pro Tyr
        580                 585                 590

Asn Ser Thr Ile Ser Leu Gln Thr Glu Tyr Leu Pro Val Ser Val Ala
    595                 600                 605

Leu Gln Met Ala Arg Gly Cys Asp His Val Leu Ala Ser Leu Val Ala
610                 615                 620

Gly Leu Glu Lys Lys Gly Val Leu Arg Pro Val Ser Thr Gly Ser Arg
625                 630                 635                 640

Leu Tyr Ser

<210> SEQ ID NO 3
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
tagctatggt cccgtactgt gcaagcttgg                                    30

<210> SEQ ID NO 4
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
atggcttgac acacaatctc ccaccacacc                                    30

<210> SEQ ID NO 5
<211> LENGTH: 30
<212> TYPE: DNA
<213> ORGANISM: ARTIFICIAL SEQUENCE

```
<220> FEATURE:
<223> OTHER INFORMATION: SYNTHETIC DNA

<400> SEQUENCE: 5
gcagcgcaac actgaccggc aaatactcgg                                30

<210> SEQ ID NO 6
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
aagagcgact tggagcagga ggcacatcgg                                30

<210> SEQ ID NO 7
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
ggtgacagac tggatccatc atgtttctta                                30

<210> SEQ ID NO 8
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
ttgtttgaac cggcatgctc tactttgtac                                30
```